(12) United States Patent
Reed, Jr.

(10) Patent No.: US 6,295,982 B1
(45) Date of Patent: Oct. 2, 2001

(54) APPARATUS FOR AND METHODS OF ADMINISTERING VOLATILE SUBSTANCES INTO AN INHALATION FLOW PATH

(76) Inventor: Fred Dewitt Reed, Jr., 8395 N Stoney Mountain Way, Flagstaff, AZ (US) 06001

( * ) Notice: Subject to any disclaimer, the term of this patent is extended or adjusted under 35 U.S.C. 154(b) by 0 days.

(21) Appl. No.: 09/355,147
(22) PCT Filed: Jul. 1, 1998
(86) PCT No.: PCT/US98/14092
§ 371 Date: Jul. 23, 1999
§ 102(e) Date: Jul. 23, 1999
(87) PCT Pub. No.: WO00/01437
PCT Pub. Date: Jan. 13, 2000
(51) Int. Cl.$^7$ ....................................... A61F 5/08
(52) U.S. Cl. .................... 128/200.24; 606/199; 424/447
(58) Field of Search ................. 128/200.24, 207.14, 128/893, 894, 888, 889; 606/199, 234, 236; 604/306; 602/58, 41–57, 59; 424/445, 446, 447, 449

(56) References Cited

U.S. PATENT DOCUMENTS

| | | | |
|---|---|---|---|
| 4,899,739 | * | 2/1990 | Konishi ................................ 128/156 |
| 5,706,800 | * | 1/1998 | Cronk et al. ..................... 128/200.24 |
| 5,890,486 | * | 4/1999 | Mitra et al. ...................... 128/200.24 |
| 6,090,403 | * | 7/2000 | Block et al. .......................... 424/447 |

\* cited by examiner

Primary Examiner—John G. Weiss
Assistant Examiner—Mital Patel
(74) Attorney, Agent, or Firm—Parsons & Goltry; Robert A. Parsons; Michael W. Goltry (57) ABSTRACT

A method of introducing a vapor (41) of a volatile substance into an inhalation flow path (24, 25) of a respiratory organ (22, 23), the method comprising the steps of providing a carrier (31, 51, 51') having a volatile substance and engaging the carrier (31, 51, 51') at the inhalation flow path (24, 25) of the respiratory organ (22, 23).

17 Claims, 5 Drawing Sheets

FIG. 15

APPARATUS FOR AND METHODS OF ADMINISTERING VOLATILE SUBSTANCES INTO AN INHALATION FLOW PATH

TECHNICAL FIELD

This invention relates generally to the field of aromatherapy and, more particularly, to vehicles for and methods of introducing a vapor of one or more volatile substances into an inhalation flow path.

BACKGROUND ART

Aromatherapy refers generally to introducing the vapor of one or more volatile substances into an inhalation flow path for inhalation into the lungs or respiratory tract. Volatile substances used in aromatherapy applications normally comprise essential volatile oils provided from, for instance, flowers, herbs and other selected plant life, fruits, etc. Because the vapor of these and other potential varieties of volatile essential oils prove to provide users with beneficial physiological and psychological benefits, aromatherapy has become increasingly popular throughout the world.

To this end, items such as pillows, earrings and other forms of jewelry, diffusers, steam vaporizers, candles, masks, soaps, ointments and salves have been devised as vehicles for containing volatile substances and for providing users with the vapor from the volatile substances. Although exemplary, these and other known vehicles for introducing the vapor from one or more volatile substances into an inhalation flow path for inhalation into the respiratory tract are obtrusive, not suitable for use except in a designated area, objectionable to people other than the user, and/or require specialized apparatus.

DISCLOSURE OF THE INVENTION

It would be highly advantageous, therefore, to remedy the foregoing and other deficiencies inherent in the prior art.

Accordingly, it is an object of the present invention to provide new and improved vehicles for and methods of introducing a vapor of one or more volatile substances into an inhalation flow path.

Another object of the present invention is to provide new and improved vehicles for introducing a vapor of one or more volatile substances into an inhalation flow path that are easy to construct.

And another object of the present invention is to provide new and improved vehicles for introducing a vapor of one or more volatile substances into an inhalation flow path that are inexpensive.

Still another object of the present invention is to provide new and improved vehicles for introducing a vapor of one or more volatile substances into an inhalation flow path that are unobtrusive during use.

Yet another object of the present invention is the provision of providing users with convenient vehicles for introducing a vapor of one or more volatile substances into an inhalation flow path that may be easily transported and used at any desired moment.

Yet still another object of the present invention is to provide a new and improved method of introducing a vapor of one or more volatile substances into an inhalation flow path that is easy to implement.

A further object of the present invention is to provide new and improved vehicles for and methods of introducing a vapor of one or more volatile substances into an inhalation flow path that are highly efficient.

BRIEF DESCRIPTION OF THE DRAWINGS

The foregoing and further and more specific objects and advantages of the instant invention will become readily apparent to those skilled in the art from the following detailed description of a preferred embodiment thereof, taken in conjunction with the drawings, in which.

BEST MODES FOR CARRYING OUT THE INVENTION

The present invention provides, among other things, improved vehicles for and methods of introducing a vapor of one or more volatile substances into an inhalation flow path of a respiratory organ. Ensuing embodiments of the invention prove exemplary for aromatherapy application that are highly efficient, unobtrusive, easy to implement and require no specialized equipment or apparatus.

Figure 1:
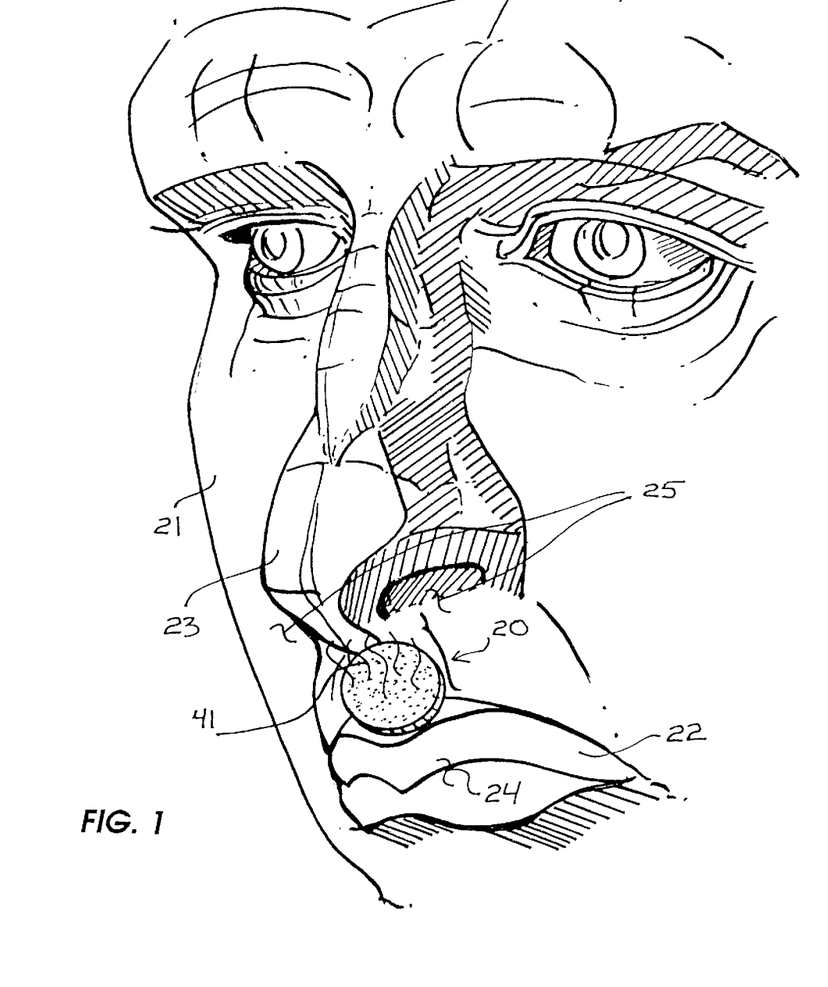
FIG. 1 is a perspective view of an embodiment of a vehicle for introducing a vapor of one or more volatile substances into an inhalation flow path, the vehicle shown as it would appear worn by a user, in accordance with the present invention.

Turning now to the drawings in which like reference characters indicate corresponding elements throughout the several views, attention is first directed to FIG. 1 illustrating a perspective view of an embodiment of a vehicle 20 for introducing a vapor of one or more volatile substances into an inhalation flow path of a user 21 as user 21 breathes. To breathe is to draw air into and expel it from the lungs or respiratory tract by way of one or more of the external respiratory organs including mouth 22 and nose 23. As air is drawn into and expelled from the lungs or respiratory tract, it is to be generally understood that the entrance of mouth 22 and entrances of nose 23 as defined by the external openings into each of the nasal passages define inhalation flow paths generally designated at 24 and 25, respectively.

Figure 2:
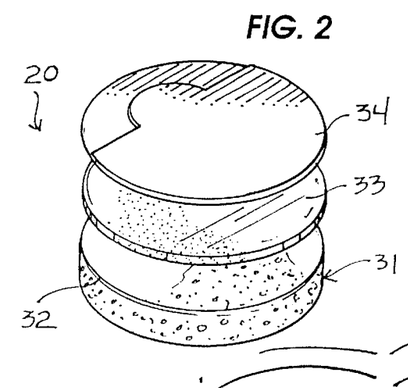
FIG. 2 is an exploded perspective view of the vehicle of FIG. 1.
Figure 3:
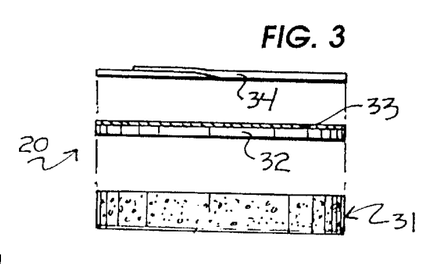
FIG. 3 is an exploded side elevational view of the vehicle of FIG. 1.

Turning to FIGS. 2 and 3, vehicle 20 is generally comprised of a series of layers including a carrier generally designated at 31, a barrier 32, an adhesive backing 33 and a cover 34 for protecting adhesive backing 33 prior to use. Carrier 31 comprises, in this specific example, a substantially disk-shaped member constructed of a natural or synthetic sponge-like or substantially absorbent material. Barrier 31 carries or is otherwise impregnated with one or more volatile substances. Because the present invention is particularly adapted for use in aromatherapy application, each of the one or more volatile substances may comprise an essential oil of one or more selected herbs, flowers and other plant life, fruits, etc. Barrier 32 is fixed to barrier 31 with, for instance, a suitable adhesive and is constructed of a metallic foil, wax paper, thin plastic or other material substantially impermeable to the one or more volatile substances carried by barrier 31. Adhesive backing 33 is carried by barrier 32 in the form of a layer with cover 34 removably carried thereon.

In operation, cover 34 may be grasp, such as by a human hand, and removed to expose adhesive backing 33. so exposed, user 21 may then engage adhesive backing 33 to his or her body proximate one or more of inhalation flow paths 24 and 25 such as, as shown in FIG. 1, adjacent the external openings of the nasal passages of nose 23. So installed, the volatility of the one or more volatile substances carried by barrier 31 will naturally emit a vapor generally designated at 41. So positioned adjacent the external openings of the nasal passages of nose 23, as user breaths into and out of nose 23, vapor 41 will introduce into inhalation path 25 permitting vapor 41 to travel into the lungs or respiratory tract as user 21 breathes thus providing user 21 with the associated beneficial effects of aromatherapy.

Barrier 32 is important for preventing the one or more volatile substances carried by barrier 31 from seeping into the adhesive layer which may not only compromise adhesive backing 33, but also cause the one or more volatile substances to contact the skin which, in some instances, may result in unwanted skin irritation. Further, because vehicle 20 is preferably worn against the skin adjacent or otherwise in one or more of inhalation paths 24 and 25, heat from the user 21 body transfers to barrier 31 which increases the volatility of the one or more volatile substances desirably enhancing the emission of vapor.

Figures 4, 5:
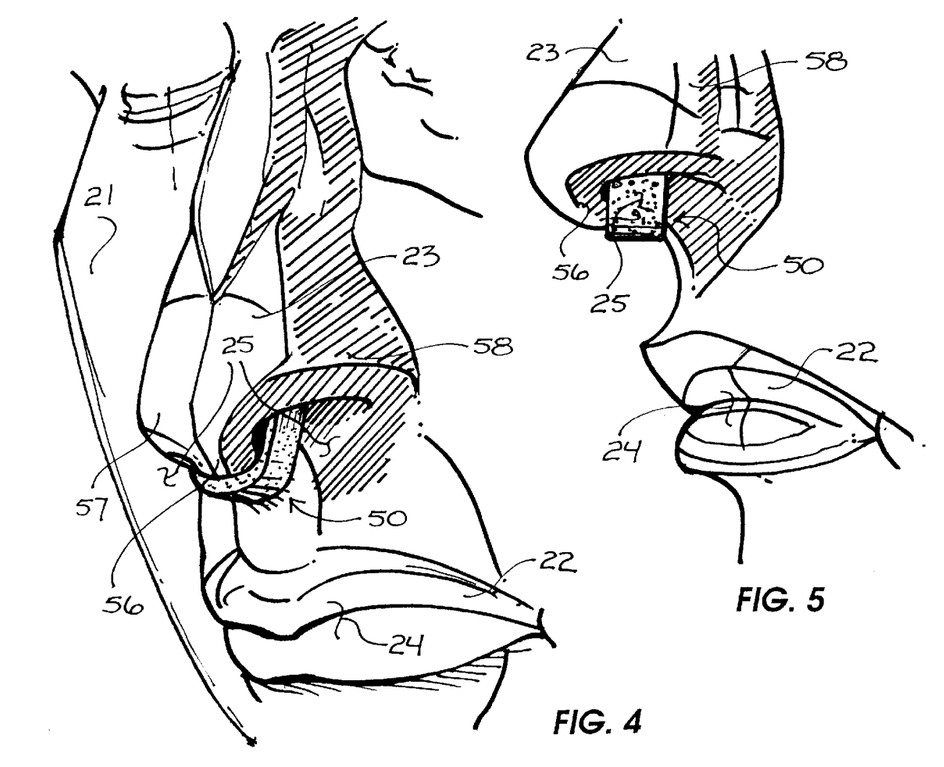
FIG. 4 is a perspective view of another embodiment of a vehicle for introducing a vapor of one or more volatile substances into an inhalation flow path, the vehicle shown as it would appear worn by a user, in accordance with the present invention.
FIG. 5 is a side elevational view of the vehicle of FIG. 4 shown as it would appear worn by the user.
Figures 6, 7, 8:
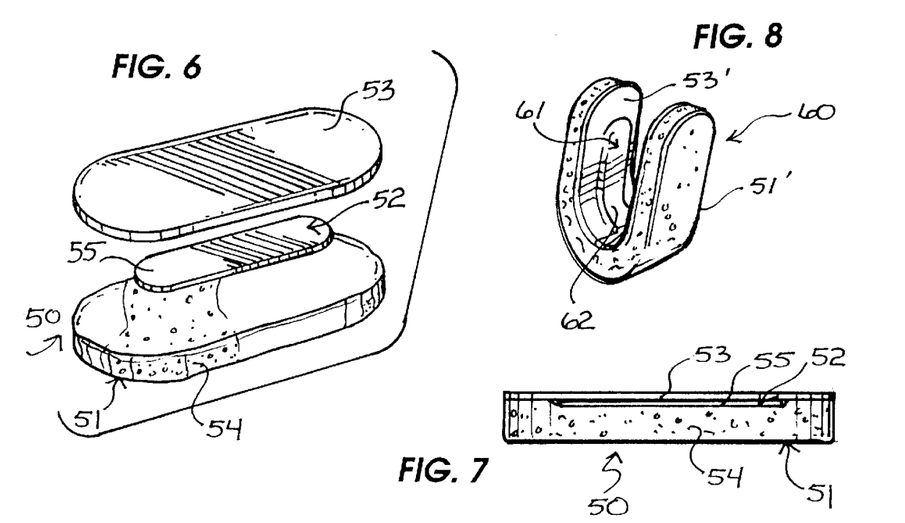
FIG. 6 is an exploded perspective view of the vehicle of FIG. 4.
FIG. 7 is a side elevational view of the vehicle of FIG. 4.
FIG. 8 is a perspective view of yet another embodiment of a vehicle for introducing a vapor of one or more volatile substances into an inhalation flow path, in accordance with the present invention.

Turning now to FIG. 4, illustrated is a perspective view of another embodiment of a vehicle 50 for introducing a vapor of one or more volatile substances into one or more of inhalation flow paths 24 and 25 of user 21. Referring to FIGS. 6 and 7, vehicle 50 is comprised of a series of layers including a carrier generally designated at 51, a clamp 52 and a barrier 53. Carrier 51 comprises, in this specific example, a substantially elongated member 54 constructed of a natural or synthetic sponge-like or substantially absorbent material. Like barrier 31, barrier 53 carries or is otherwise impregnated with one or more volatile substances. Barrier 53 captures clamp 52 against barrier 53 and is fixed to member 54 with, for instance, a suitable adhesive. Barrier 53, of which is provided in the form of a layer covering barrier 53, is preferably constructed of a metallic foil, wax paper, thin plastic or other material substantially impermeable to the one or more volatile substances carried by barrier 53. In this specific example, clamp 52 comprises a deformable member 55 constructed of, for instance, a deformable or malleable metal.

In operation, vehicle 50 may be grasp, such as by a human hand, positioned and deformed against septum 56 to clamp vehicle 50 against septum 56 of nose 23 in inhalation flow path 25 as shown substantially in FIGS. 4 and 5. Deformable member 55 thus permits the clamping of vehicle 50 against not only septum 56, but also to the external sidewalls 57 and 58 of nose bounding the external openings into the nasal passages if so desired. So installed, the volatility of the one or more volatile substances carried by barrier 53 will naturally emit a vapor which will introduce into inhalation flow path 25 to be carried into the lungs or respiratory tract as user 21 breathes. Like barrier 32, barrier 53 is important for preventing the one or more volatile substances carried by barrier 53 from contacting the skin or nasal membranes which, in some instances, may result in unwanted skin and/or nasal membrane irritation.

Referring now to FIG. 8, illustrated is a perspective view of yet another embodiment of a vehicle 60 for introducing a vapor of one or more volatile substances into an inhalation flow path, in accordance with the present invention. Vehicle 60 is substantially identical in structure and function to vehicle 50. Therefore, reference characters used to describe vehicle 50 will also be used to describe vehicle 60 to the extent of the common structural features. However, in the interests of clarity, common reference characters used to describe vehicle 50 will include a prime ("'") symbol.

In this regard, and like vehicle 50, vehicle 60 includes carrier 51', barrier 53' and a clamp 61 captured between carrier 51' and barrier 53'. In this embodiment, clamp 61 comprises a substantially U-shaped clip constructed of a selected metal, plastic or other material having shape memory. Clamp 61 permits the clipping engagement of vehicle 50 against, for instance, one of at least the septum and external sidewalls bounding the external openings of the nasal passages of the nose of a user.

Carriers 31, 51 and 51' may be provided or otherwise impregnated with one or more volatile substances in a variety of manners, not the least of which may include impregnation during manufacture. As an alternative, vehicle 20, like vehicles 50 and 60, may be housed in one of plurality of assemblages suitable for allowing the selective and desired impregnation of carrier 31 as desired prior to use.

Figures 9, 10, 11:
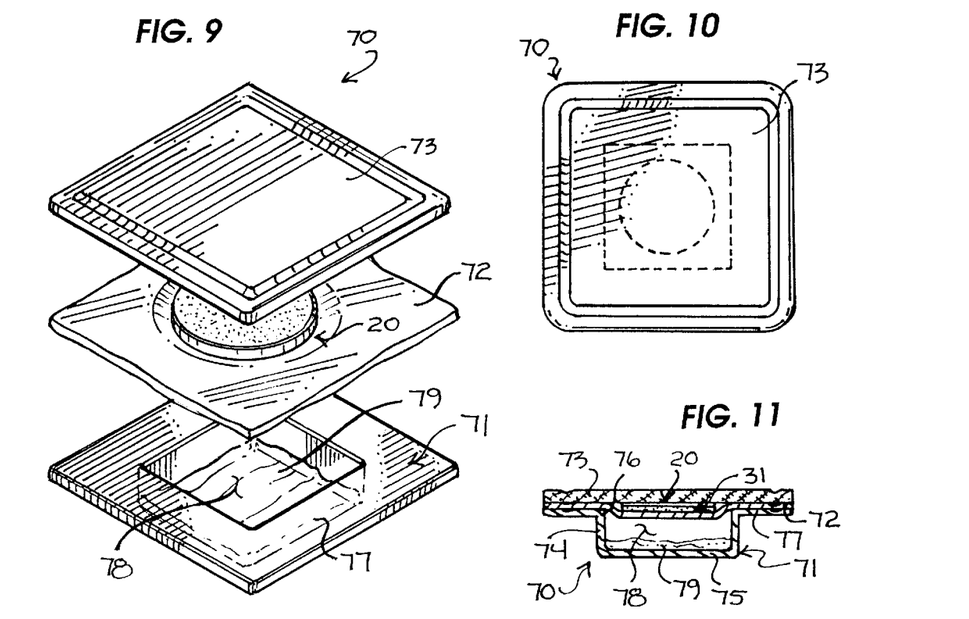
FIG. 9 is an exploded perspective view of an assembly for providing the vehicle of FIG. 1 with one or more volatile substances, in accordance with the present invention.
FIG. 10 is a top elevational view of the assembly of FIG. 9.
FIG. 11 is a vertical sectional view of the vehicle of FIG. 9.

With this in mind, attention is first directed to FIG. 9 illustrating an exploded perspective view of an assembly 70 for providing vehicle 20 with one or more volatile substances, in accordance with the present invention. With additional reference to FIG. 11 illustrating a vertical sectional view of assembly 70, assembly 70 includes a receptacle 71, a rupturable or tearable layer 72 and a cover 73 (also shown in FIG. 10). Regarding FIG. 11, receptacle 71 includes a continuous sidewall 74 having a closed end 75 and an open end 76 with a continuous flange 77 extending outwardly from open end 76. Continuous sidewall 74 and closed end 75 cooperate to bound a chamber 78 in which is contained one or more volatile substances 79.

Preferably constructed a selected metal foil, wax paper or other similar material that may be easily torn or ruptured, rupturable layer 72 is fixed, such as with a selected adhesive, to continuous flange 77 occluding open end 76 and enclosing chamber 78. Cover 73, of which may be constructed of paper, plastic or other selected material, is fixed, such as with a selected adhesive, to rupturable layer 72 capturing vehicle 20 therebetween proximate open end 76.

With receptacle 71 preferably constructed of a thin plastic or other deformable material, assembly 70 may be grasp, such as with a human hand, and at least one of closed end 75 and cover 73 compressed inwardly to tear or rupture rupturable layer 72 at open end 76 to expose vehicle 20 to the one or more volatile substances carried in chamber 78 to permit the one or more volatile substances to contact and impregnate carrier 31. So impregnated, cover 73 may be grasp, such as with a human hand, and peeled away to allow the user to remove vehicle 20 from assembly 70. Upon removal, the user may then install vehicle 20 as previously discussed for normal operation.

Figures 12, 13:
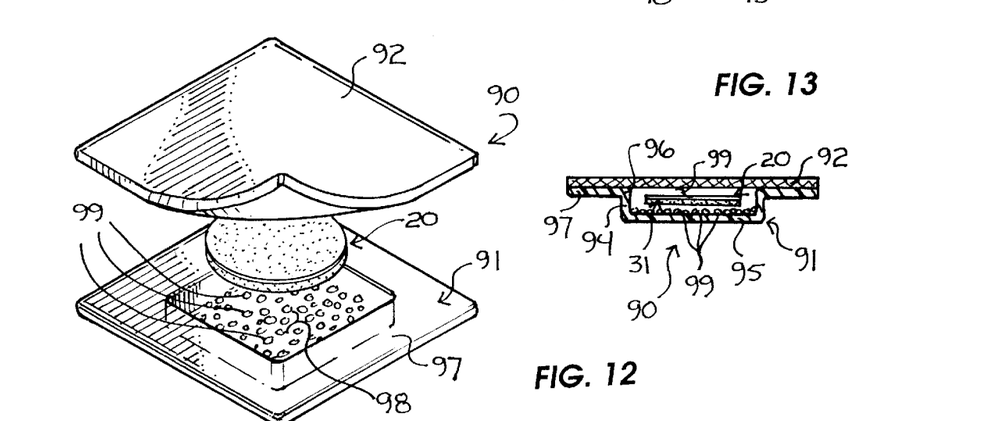
FIG. 12 is an exploded perspective view of another assembly for providing the vehicle of FIG. 1 with one or more volatile substances, in accordance with the present invention.
FIG. 13 is a vertical sectional view of the vehicle of FIG. 12.

With attention directed FIG. 12, illustrated is an exploded perspective view of another assembly 90 for providing vehicle 20 with one or more volatile substances, in accordance with the present invention. With additional reference to FIG. 13 illustrating a vertical sectional view of assembly 90, assembly 90 includes a receptacle 91 and a cover 92. Regarding FIG. 13, receptacle 91 includes a continuous sidewall 94 having a closed end 95 and an open end 96 with a continuous flange 97 extending outwardly from open end 96. Continuous sidewall 94 and closed end 95 cooperate to bound a chamber 98 in which is contained microcapsules 99 each containing one or more volatile substances. Cover 92, of which may be constructed of paper, plastic or other selected material, is fixed, such as with a selected adhesive, to continuous flange 97 occluding open end 96 enclosing chamber 98 to contain microcapsules 99 and vehicle 20 therein.

With receptacle 91 preferably constructed of a thin plastic or other deformable material, assembly 90 may be grasp, such as with a human hand, and at least one of closed end 95 and cover 92 compressed inwardly to rupture microcapsules 99 to release and expose carrier 31 of vehicle 20 to the one or more volatile substances contained therein thereby permitting the one or more volatile substances to contact and impregnate carrier 31. So impregnated, cover 92 may be grasp, such as with a human hand, and peeled away to allow the user to remove vehicle 20 from assembly 90. Upon removal, the user may then install vehicle 20 as previously discussed for normal operation.

Microcapsules 99 are each of a conventional type comprising a closed outer wall containing one or more volatile substances therein. In accordance with conventional microcapsules, the closed outer wall may be constructed of cellulose or other material that may be easily ruptured upon compression. Furthermore, although chamber 98 of assembly 90 is shown containing microcapsules, one or more macrocapsules, such as macrocapsule 100, of substantially identical yet larger construction to each of microcapsules 99 and containing one or more volatile substances may be used if so desired.

Figure 14:
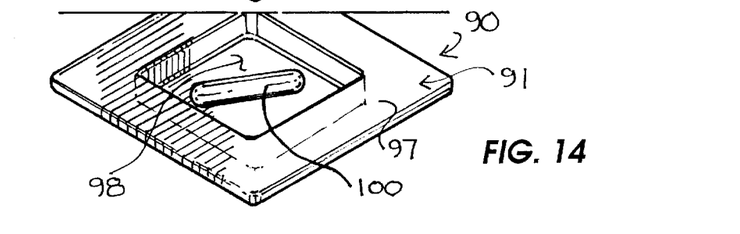
FIG. 14 is a perspective view of a receptacle of the assembly of FIGS. 12 and 13 and a macrocapsule contained by the receptacle.
Figure 15:
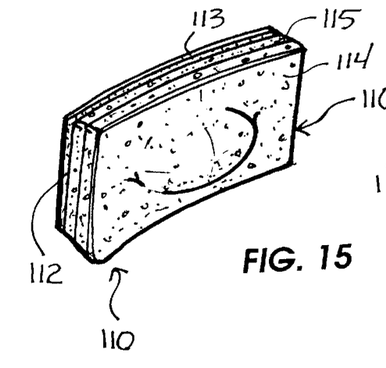
FIG. 15 is a perspective view of yet still another embodiment of a vehicle for introducing a vapor of one or more volatile substances into an inhalation flow path, in accordance with the present invention.
Figure 16:
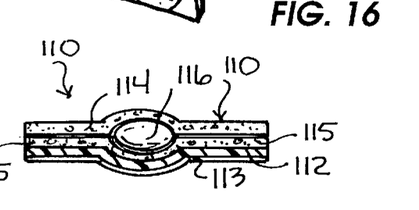
FIG. 16 is a vertical sectional view of the vehicle of FIG. 15.

Turning now to FIGS. 15 and 16, illustrated is yet still another embodiment of a vehicle 110 for introducing a vapor of one or more volatile substances into an inhalation flow path, in accordance with the present invention. Vehicle 110 is comprised of a series of layers including a carrier generally designated at 111, a barrier 112 fixed to carrier 111 such as with a suitable adhesive, and an adhesive backing 113 carried by barrier 112 in the form of a layer. Carrier 111 comprises, in this specific example, a pair of members 114 and 115 sandwiched together with a suitable adhesive and each constructed of a natural or synthetic sponge-like or substantially absorbent material. Captured between members 114 and 115 is a macrocapsule 116 containing one or more volatile substances, macrocapsule 116 being of substantially similar construction to macrocapsule 100 discussed previously in combination with FIG. 14.

In operation, vehicle 110 may be grasp, such as with a human hand, and compressed to rupture macrocapsule 116 to release and permit the one or more volatile substances contained therein to impregnate members 114 and 115. Barrier 112, of which is provided in the form of a layer covering, in this specific example, member 115, is preferably constructed of a metallic foil, wax paper, thin plastic or other material substantially impermeable to the one or more volatile substances impregnated into and through each of the members 114 and 115. After release of the one or more volatile substances into and through members 114 and 115, vehicle 110 may be adhesively engaged to a user for aromatherapy in much the same fashion as vehicle 20 discussed previously.

Rather than, or in addition to, adhesive backing 113, vehicle 110 may be provided with one of previously discussed clamp 52 and clamp 61 if so desired for permitting clamping engagement of vehicle 110 to a user if so desired. Furthermore, and although not shown in FIGS. 15 and 16, vehicle 110 may be provided with a removable cover to protect adhesive backing 113 prior to use. Additionally, microcapsules may be used in lieu of macrocapsule 116 if so desired.

Figure 17:
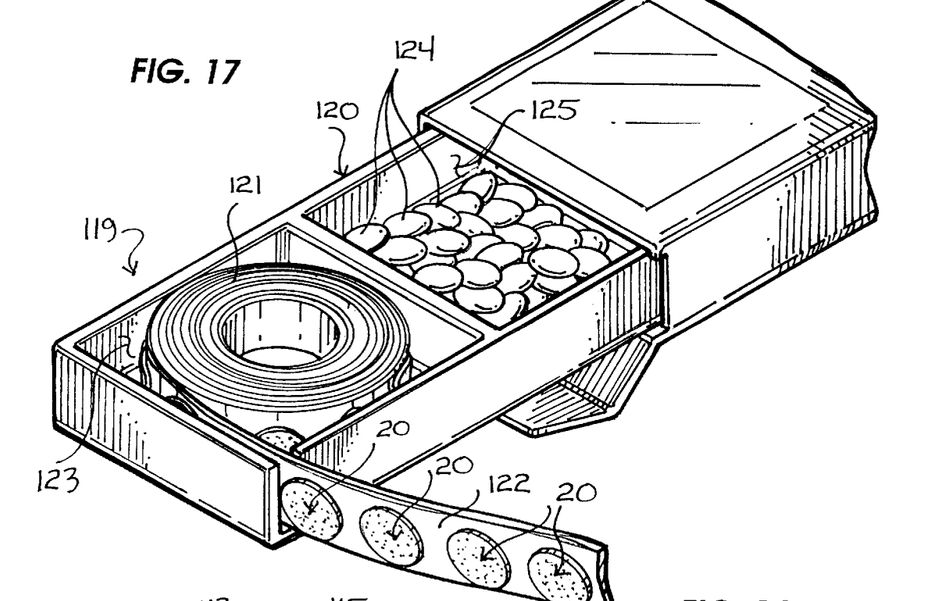
FIG. 17 is a perspective view of a container housing a plurality of vehicles carried by a roll of sheet material and a plurality of capsules each containing one or more volatile substances, in accordance with the present invention.

In accordance with preferred teachings, it may be desirable to provide users with a convenient and portable packaging assembly that may be carried, such as in a pocket, purse, etc., and employed when desired for aromatherapy. To this end, and with attention directed to FIG. 17, illustrated is a perspective view of a packaging assembly 119. In this specific embodiment, packaging assembly 119 includes a container 120 housing a plurality of vehicles 20 first set forth in FIG. 1. The vehicles 20 are carried by, such as with a suitable adhesive, a roll 121 of sheet material 122 in a first compartment 123. Further included is a plurality of capsules 124 each containing one or more volatile substances carried in a second compartment 125 of container 120. Each one of the capsules 124 is of substantially identical construction to each of macrocapsules 100 and 116 discussed previously, further details of which will not be further addressed.

Figures 18, 19, 20, 21, 22:
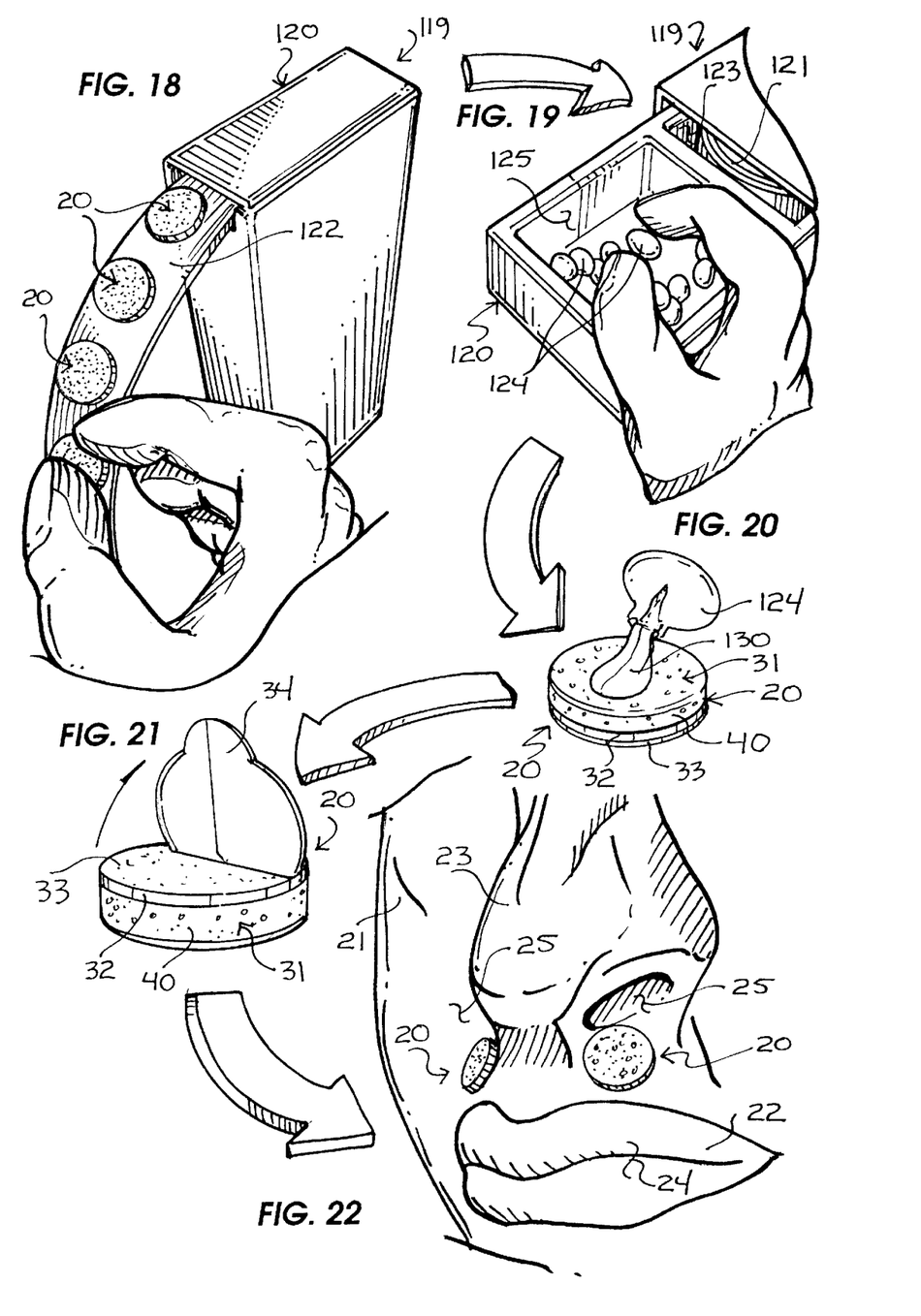
FIGS. 18 through 22 illustrate a sequence of steps of providing the vehicles of FIG. 18 with one or more volatile substances from one or more of a plurality of capsules and for introducing a vapor from one or more of the volatile substances into an inhalation flow path, in accordance with the present invention.

In operation, one of vehicles 20 may be grasp, such as with a human hand, and removed from the sheet material 122 as shown in FIG. 18. One of capsules 124 may then be grasp such as with a human hand as shown in FIG. 19 and, while being held adjacent member 40 of vehicle as shown in FIG. 20, squeezed to an extent sufficient to rupture capsule 124 to dispense the one or more volatile substances 130 contained therein onto member 40 to permit the one or more volatile substances to impregnate into and through member 40. After impregnation, cover 34 may be peeled away to expose adhesive backing 33 as shown in FIG. 21 and vehicle 20 then adhesively secured to user 21 for aromatherapy in the manner previously discussed in connection with FIG. 1. Regarding FIG. 22, shown are a pair of vehicles 20 having been prepared in accordance with the method set forth in FIGS. 18–21 and installed with user 21 in spaced relation adjacent the external openings of the nasal passages of nose 23 at inhalation flow path 25. Although the method set forth in FIGS. 18–22 have been discussed in combination with vehicle 20, the method may also be readily implemented with vehicles 50 and 60 if desired.

In summary, the present invention provides exemplary vehicles and methodologies for introducing a vapor of one or more volatile substances into an inhalation flow path of a respiratory organ in aromatherapy application. Foregoing embodiments of the present invention are easy to construct, and provide a variety of means for providing or otherwise impregnating a selected vehicle with one or more volatile substances. In this regard, the various embodiments are not only convenient, but also permit users to easily transport aromatherapy vehicles for selective and desired use as needed without having to employ specialized equipment.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A method of introducing a vapor of at least one volatile substance into an inhalation flow path of a respiratory organ, the method comprising the steps of:
   providing a carrier conformable to a surface of skin;
   providing the carrier with at least one volatile substance;
   providing a barrier coupled to a surface of the carrier, the barrier being substantially impermeable to the one or more volatile substances carried by the carrier; and
   engaging the carrier to the surface of skin proximate an inhalation flow path of a respiratory organ with the barrier adapted to be interposed between the carrier and the skin to prevent the one or more volatile substances from contacting the skin.

2. The method of claim 1, wherein the step of providing a carrier further includes the steps of providing a substantially absorbent member.

3. The method of claim 1, wherein the step of providing the carrier with at least one volatile substance further includes the step of impregnating the carrier with at least one volatile substance.

4. The method of claim 3, wherein the step of impregnating the carrier with at least one volatile substance further includes the steps of:
   providing a rupturable capsule containing at least one volatile substance;
   embedding the rupturable capsule in the carrier; and
   rupturing the rupturable capsule.

5. The method of claim 3, wherein the step of impregnating the carrier with at least one volatile substance further includes the step of dispensing one or more volatile substance onto the carrier.

6. The method of claim 1, wherein the step of engaging the carrier proximate an inhalation flow path further includes the step of adhesively engaging the carrier proximate the inhalation flow path of the respiratory organ.

7. The method of claim 1, wherein the step of engaging the carrier proximate an inhalation flow path further includes the step clamping the carrier to the respiratory organ proximate the inhalation flow path.

8. The method of claim 7, wherein the step of clamping the carrier to the respiratory organ proximate the inhalation flow path further includes the steps of:
   providing a clamp;
   coupling the clamp to the carrier; and
   engaging the clamp to the respiratory organ.

9. The method of claim 8, wherein the step of coupling the clamp to the carrier further includes the step of adhesively coupling the clamp to the carrier.

10. The method of claim 8, wherein the steps of providing a clamp and engaging the clamp to the respiratory organ further includes the steps of:
    providing a deformable element; and
    deforming the deformable element against the respiratory organ.

11. A vehicle for introducing a vapor of one at least one volatile substance into an inhalation flow path of a respiratory organ, the vehicle comprising:
    a carrier conformable to a surface of skin;
    at least one volatile substance carried by the carrier;
    a barrier coupled to a surface of the carrier, the barrier being substantially impermeable to the at least one volatile substances carried by the carrier; and
    means for engaging the carrier is a surface of skin proximate an inhalation flow path of the respiratory organ with the barrier adapted to be interposed between the carrier and the surface of skin to prevent the at least one volatile substances from contacting the skin.

12. The vehicle of claim 11, wherein the carrier includes a substantially absorbent member.

13. The vehicle of claim 11, wherein the means includes adhesive carried by the barrier, the barrier dividing the carrier from the adhesive backing.

14. The vehicle of claim 11, further including a barrier dividing the carrier from the adhesive backing, the barrier being substantially impermeable to the one or more volatile substances carried by the carrier.

15. The vehicle of claim 11, wherein the means includes a deformable element deformably engagable against the respiratory organ.

16. The vehicle of claim 11, wherein the means includes a clip clippingly engagable against the respiratory organ.

17. The vehicle of claim 11, wherein the at least one volatile substance carried by the carrier is carried in a rupturable capsule embedded in the carrier.

* * * * *

UNITED STATES PATENT AND TRADEMARK OFFICE
CERTIFICATE OF CORRECTION

PATENT NO.     : 6,295,982 B1
DATED          : October 2, 2001
INVENTOR(S)    : Fred Dewitt Reed, Jr.

It is certified that error appears in the above-identified patent and that said Letters Patent is hereby corrected as shown below:

<u>Column 8,</u>
Line 37, replace "is" with -- to --.

Signed and Sealed this

Twentieth Day of August, 2002

Attest:

JAMES E. ROGAN
*Attesting Officer*    *Director of the United States Patent and Trademark Office*